United States Patent [19]

Suda et al.

[11] Patent Number: 5,061,695
[45] Date of Patent: Oct. 29, 1991

[54] ANTITUMOR SUBSTANCE BE-12406

[75] Inventors: Hiroyuki Suda; Katuhisa Kojiri; Akira Okura, all of Tokyo; Koutaro Funaishi; Kenji Kawamura, both of Aichi; Masanori Okanishi, Tokyo, all of Japan

[73] Assignee: Banyu Pharmaceutical Co., Ltd., Tokyo, Japan

[21] Appl. No.: 476,065

[22] Filed: Jan. 30, 1990

[30] Foreign Application Priority Data

Jan. 30, 1989 [JP] Japan .................................... 1-19978
Dec. 12, 1989 [JP] Japan .................................... 1-322280

[51] Int. Cl.$^5$ .................... A61K 31/70; C07H 17/04; C07D 311/02
[52] U.S. Cl. ........................................ 514/28; 514/53; 514/64; 514/453; 536/4.1; 536/17.1; 536/18.1; 549/213; 549/384; 549/278
[58] Field of Search ...................... 536/17.8, 18.1, 4.1; 549/213, 384, 278; 514/28, 53, 64, 453

[56] References Cited

U.S. PATENT DOCUMENTS 4,105,778  8/1978  Philipp et al. .................. 549/384 X
4,760,136  7/1988  Mori et al. ..................... 536/18.1 X

FOREIGN PATENT DOCUMENTS 1431733  2/1966  France ............................... 549/384

Primary Examiner—Catherine S. K. Scalzo
Attorney, Agent, or Firm—Sughrue, Mion, Zinn Macpeak & Seas

[57] ABSTRACT

An antitumor substance BE-12406 or a pharmaceutically acceptable salt thereof, which is represented by the general formula

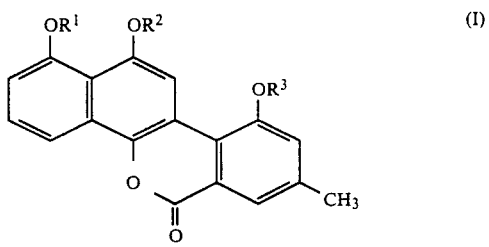

and a method of producing the novel substance.

6 Claims, No Drawings

ANTITUMOR SUBSTANCE BE-12406

FIELD OF THE INVENTION

The present invention relates to a novel substance which is of value in the field of medicine. More particularly, the invention relates to a novel substance which inhibits the growth and proliferation of tumor cells to produce an antitumor effect, a method of producing the novel substance, uses for the substance, and a novel microorganism which produces the substance.

BACKGROUND OF THE INVENTION

In the field of cancer chemotherapy, a variety of microbial metabolites such as bleomycins or adriamycin have been used in clinical practice. However, many of these substances are not sufficiently effective for many of the tumors which are clinically encountered and, moreover, the acquisition of resistance of tumor cells to these drugs, which is being made increasingly clear, has been interfering with their use in clinical cases (the Proceedings of the 47th Congress of the Japanese Cancer Association, pages 12 to 15, 1988).

Under the circumstances, there is naturally a constant demand for the development of new anticancer agents. Thus, a strong demand exists for a substance which would overcome the resistance of various types of tumors to the existing anticancer agents and be effective even in those cases which do not respond to the anticancer drugs heretofore available.

The inventors of the present invention screened a variety of microbial metabolites in search of candidate antitumor agents. As a result, it has been found that a novel compound of the following general formula (I) have excellent antitumor activity. The present invention has been achieved on the basis of the above finding.

SUMMARY OF THE INVENTION

The present invention is, therefore, directed to a novel antitumor substance, designated as BE-12406 herein, which has the general formula

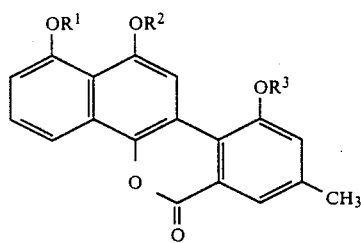

wherein $R^1$ and $R^2$, which may be the same or different, each represents a hydrogen atom or a group of the formula

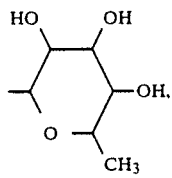

and $R^3$ represents a hydrogen atom or a methyl group, or a pharmaceutically acceptable salt thereof.

In further aspects, the present invention relates to a method of producing the antitumor substance BE-12406, use of the substance BE-12406 as an antitumor agent, and a microorganism which produces the substance BE-12406.

The antitumor substance BE-12406 according to the present invention is preferably BE-12406A, B, $X_1$ and $X_2$ which are respectively defined hereunder.

The compound of the general formula (I) wherein $R^1$ is a hydrogen atom, $R^2$ is a group of the formula

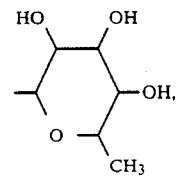

and $R^3$ is a methyl group is referred to as BE-12406A.

The compound of the general formula (I) wherein $R^1$ is a hydrogen atom, $R^2$ is a group of the formula

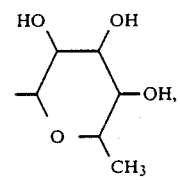

and $R^3$ is a hydrogen atom is referred to as BE-12406B.

The compound of the general formula (I) wherein $R^1$ is a group of the formula

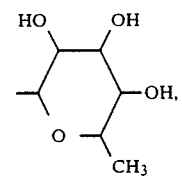

$R^2$ is a hydrogen atom, and $R^3$ is a methyl group is referred to as BE-12406$X_1$.

The compound of the general formula (I) wherein $R^1$ is a hydrogen atom, $R^2$ is a hydrogen atom, and $R^3$ is a methyl group is referred to as BE-12406$X_2$.

DETAILED DESCRIPTION OF THE INVENTION

The physicochemical information on these compounds of the present invention is presented below.

Physicochemical Properties of BE-12406A

Description: a light yellow amorphous solid or crystal

Molecular formula: $C_{25}H_{24}O_9$

Analysis: Calcd. C, 64.10%; H, 5.16%. Found C, 64.04%; H, 5.19%.

Solubility: Sparingly soluble in water and readily soluble in tetrahydrofuran, dimethyl sulfoxide and other organic solvents.

Acidity/neutrality/basicity: Neutral.

Rf: 0.60 (developer: chloroform/methanol (5:1 v/v)) 0.36 (developer: chloroform/methanol/aqueous ammonia (50:10:1 v/v)), (Kieselgel 60 $F_{254}$, Merck).

Melting point: 238° to 243° C. (decomp.)

Color reactions: Potassium permanganate: positive, anisaldehyde - sulfuric acid: positive.

Mass spectrum (FAB-MS): 469 [M+H]+.

Ultraviolet absorption spectrum ($\lambda_{max}$ in methanol) nm: 243, 264, 273, 300, 310, 324, 338, 375.

Infrared absorption spectrum (KBr tablet) cm$^{-1}$: 3420, 2930, 1700, 1625, 1595, 1390, 1250, 1145, 1050, 960, 805, 790.

$^1$H-NMR (DMSO-d$_6$) δ ppm: 1.25 (d, 3H), 2.50 (s, 3H), 3.39 (m, 1H), 3.78 (m, 1H), 3.80 (m, 1H), 4.06 (s, 3H), 4.10 (m, 1H), 4.85 (brd, 1H), 4.95 (brd, 1H), 5.13 (brd, 1H), 5.39 (d, 1H), 7.00 (d, 1H), 7.48 (brs, 1H), 7.49 (t, 1H), 7.78 (brs, 1H), 7.85 (d, 1H), 8.70 (s, 1H), 9.75 (brs, 1H).

$^{13}$C-NMR (DMSO-d$_6$) δ ppm: 17.7, 21.0, 56.1, 69.8, 70.0, 70.5, 71.7, 101.5, 109.5, 111.8, 112.0, 112.6, 115.8, 118.8, 120.4, 121.5, 122.0, 125.5, 127.7, 140.0, 140.6, 148.4, 153.4, 156,6, 159.7.

Physicochemical Properties of BE-12406B

Description: a light yellow amorphous solid or crystal.

Molecular formula: $C_{24}H_{22}O_9$

Analysis: Calcd. C. 63.43%; H, 4.88%. Found C, 63.21%; H, 4.90%.

Solubility: Sparingly soluble in water and readily soluble in tetrahydrofuran, dimethyl sulfoxide and other organic solvents.

Acidity/neutrality/basicity: Neutral.

Rf: 0.34 (developer: chloroform/methanol (5:1 v/v)) 0.36 (developer: chloroform/methanol/aqueous ammonia (50:10:1 v/v)), (Kieselgel 60 F$_{254}$, Merck)).

Melting point: 230° to 235° C. (decomp.).

Color reactions: Potassium permanganate: positive, anisaldehyde - sulfuric acid: positive.

Mass spectrum (FAB-MS): 455 [M+H]+.

Ultraviolet absorption spectrum ($\lambda_{max}$ in methanol) nm: 244, 264, 273, 325, 340, 375.

Infrared absorption spectrum (KBr tablet) cm$^{-1}$: 3420, 1700, 1625, 1595, 1390, 1340, 1140, 1050, 960, 790.

$^1$H-NMR (DMSO-d$_6$) δ ppm: 1.23 (d, 3H), 2.42 (s, 3H), 3.39 (m, 1H), 3.78 (m, 1H), 3.80 (m, 1H), 4.10 (m, 1H), 5.39 (d, 1H), 6.98 (d, 1H), 7.29 (brs, 1H), 7.49 (t, 1H), 7.69 (brs, 1H), 7.85 (d, 1H), 8.86 (s, 1H), 9.75 (brs, 1H), 11.07 (brs, 1H).

$^{13}$C-NMR (DMSO-d$_6$) δ ppm: 17.8, 20.8, 70.0, 70.1, 70.7, 71.8, 101.2, 110.1, 111.7, 112.0, 113.5, 115.9, 118.9, 120.7, 122.3, 122.9, 125.8, 127.8, 139.8, 140.5, 148.4, 153.7, 155.6, 160.2.

Physicochemical Properties of BE-12406X$_1$

Description: a light yellow amorphous solid or crystal

Molecular formula: $C_{25}H_{24}O_9$.

Analysis: Calcd. C, 64.10%; H, 5.16%. Found C, 63.98%; H, 5.21%.

Solubility: Sparingly soluble in water and soluble in dimethylformamide, dimethyl sulfoxide and other organic solvents.

Acidity/neutrality/basicity: Neutral.

Rf: 0.60 (developer: chloroform/methanol (5:1 v/v)) 0.16 (developer: chloroform/methanol/aqueous ammonia (50:10:1 v/v)), (Kieselgel 60 F$_{254}$, Merck).

Color reactions: Potassium permanganate: positive.

Mass spectrum (FAB-MS): 469 [M+H]+.

Ultraviolet absorption spectrum ($\lambda_{max}$ in methanol) nm: 242, 265, 274, 310, 327, 340, 380.

Infrared absorption spectrum (KBr tablet) cm$^{-1}$: 3410, 1705, 1620, 1390, 1335, 1240, 1140, 1100, 1070, 1050, 980, 940, 780.

$^1$H-NMR (DMSO-d$_6$) δ ppm: 1.16 (d, 3H), 2.49 (s, 3H), 3.37 (t, 1H), 3.65 (m, 1H), 3.79 (dd, 1H), 4.07 (s, 3H), 4.07 (m, 1H), 5.57 (d, 1H), 7.26 (d, 1H), 7.47 (brs, 1H), 7.55 (t, 1H), 7.78 (brs, 1H), 8.02 (d, 1H), 8.37 (s, 1H), 9.45 (brs, 1H).

$^{13}$C-NMR (DMSO-d$_6$) δ ppm: 17.8, 21.1, 56.2, 69.9, 70.0, 70.5, 71.7, 100, 106.8, 111.9, 113.6, 115.2, 115.6, 118.7, 120.4, 121.5, 122.2, 125.3, 127.0, 138.1, 140.0, 149.2, 152.3, 156.8, 159.8.

Physicochemical Properties of BE-12406X$_2$

Description: a light yellow amorphous solid or crystal.

Molecular formula: $C_{19}H_{14}O_5$.

Analysis: Calcd. C, 70.80%; H, 4.38%. Found C, 70.68%; H, 4.25%.

Solubility: Sparingly soluble in water and soluble in dimethylformamide, dimethyl sulfoxide and other organic solvents.

Acidity/neutrality/basicity: Neutral.

Rf: 0.86 (developer: chloroform/methanol (5:1 v/v)) 0.40 (developer: chloroform/methanol/aqueous ammonia (50:10:1 v/v)), (Kieselgel 60 F$_{254}$, Merck).

Melting point: No definite melting point up to 270° C.

Color reactions: Potassium permanganate: positive.

Mass spectrum (FAB-MS): 323 [M+H]+.

Ultraviolet absorption spectrum ($\lambda_{max}$ in methanol) nm: 242, 265, 274, 305, 327, 343, 383.

Infrared absorption spectrum (KBr tablet) cm$^{-1}$: 1670, 1620, 1590, 1395, 1370, 1300, 1250, 1160, 1120, 1050, 980, 800, 750, 640.

$^1$H-NMR (DMSO-d$_6$) δ ppm: 2.50 (s, 3H), 4.08 (s, 3H), 6.92 (d, 1H), 7.48 (s, 1H), 7.48 (t, 1H), 7.79 (brs, 1H), 7.80 (d, 1H), 8.30 (s, 1H), 10.95 (brs, 1H).

$^{13}$C-NMR (DMSO-d$_6$) δ ppm: 21.0, 56.3, 105.3, 110.5, 112.4, 113.6, 114.1, 119.0, 120.8, 121.7, 122.9, 125.3, 128.1, 138.8, 140.2, 149.6, 154.0, 157.0, 160.1.

The retention times of the above four compounds, namely BE-12406A, B, X$_1$ and X$_2$, in high performance liquid chromatography (Capcell Pack C18, 4.6 mm×250 mm, Shiseido Co., Ltd.; mobile phase, methanol-water (75:25); flow rate, 1 ml/min.; detection, UV (242 nm)) were 8.58, 6.48, 7.60 and 10.88 minutes, respectively.

Biological Activity of BE-12406A, B, X$_1$ and X$_2$

In vitro activity tests were performed for evaluating the inhibitory activities of the antitumor substances BE-12406A and B against mouse tumor cells. In the in vitro antitumor assay using P388 tumor cells, the antitumor substance BE-12406A or B was first dissolved in dimethyl sulfoxide and the solution was serially diluted with a cell culture medium containing 20% of dimethyl sulfoxide (20% DMSO-RPMI-1640 medium). Then, 2 μl of each dilution was added to 200 μl of a cell culture medium (10% fetal calf serum-RPMI-1640 medium) containing 2.5×10$^4$ tumor cells and the mixture was incubated under 5% CO$_2$ at 37° C. for 72 hours. The viable cells were then counted with a Coulter counter. The result was compared with the control data. As a result, both BE-12406A and B were found to markedly inhibit the growth of P388 tumor cells and their concentrations (IC$_{50}$) causing 50% inhibition of P388/S cell growth were 0.8 and 7 μM, respectively. The corresponding values for P388/V cells were 0.2 and 7 μM, respectively.

The P388/S tumor cell line is one of the common mouse leukemia cell lines, and the P388/V line is a strain of P388 leukemia cell which has acquired resistance to the anticancer agent vincristine.

Furthermore, BE-12406A and B inhibited the P388/A cells which had acquired resistance to the anticancer agent adriamycin and their 50% inhibitory concentrations ($IC_{50}$) were 0.9 and 11 μM, respectively. The above results are summarized in Table 1.

TABLE 1

| Tumor Cells | $IC_{50}$ (μM) | |
|---|---|---|
| | BE-12406A | BE-12406B |
| P388/S | 0.8 | 7 |
| P388/V | 0.2 | 7 |
| P388/A | 0.9 | 11 |

Then, the in vitro inhibitory activity of BE-12406A and B was assayed using HeLa cells, which are human cancer cells, and L1210 cells which are mouse leukemia cells.

Thus, antitumor substance BE-12406A or B in a concentration series was added to 200 μl of a cell culture medium (10% fetal calf serum-MEM medium) containing $4 \times 10^3$ HeLa cells and the mixture was incubated under 5% $CO_2$ at 37° C. for 72 hours. The surviving adherent cells were fixed with 10% formalin and stained with 0.01% Crystal Violet. Using a 1:1 (v/v) mixture of ethylene glycol and ethanol, the dye was extracted from the stained cells and the absorbance at 590 nm was measured and compared with the control. Both BE-12406A and B inhibited growth of HeLa cells and their 50% inhibitory concentrations ($IC_{50}$) were 11 and 20 μM, respectively.

The growth inhibition assay using L1210 cells was performed as follows. Thus, antitumor substance BE-12406A or B in a concentration series was added to 200 μl of a cell culture medium (10% fetal calf serum-RPMI-1640) containing $4.5 \times 10^3$ L1210 cells and the mixture was incubated under 5% $CO_2$ at 37° C. for 72 hours. The surviving suspended cells were counted with a Coulter counter and the result was compared with the control. Both BE-12406A and B inhibited growth of L1210 cells and their 50% inhibitory concentrations ($IC_{50}$) were 9.6 and 60 μM, respectively. The above results are summarized in Table 2.

TABLE 2

| Tumor Cells | $IC_{50}$ (μM) | |
|---|---|---|
| | BE-12406A | BE-12406B |
| HeLa | 11 | 20 |
| L1210 | 9.6 | 60 |

The antitumor substance BE-12406A of the invention showed an antitumor effect on transplanted mouse S-180 tumor cells (ascites type). In this assay using mice, $10^6$ (lethal dose) S-180 tumor cells pre mouse were intrapetitoneally administered and the 5% DMSO-PBS (phosphate Buffered Saline solution of BE-12406A in a dilution series (1:2, 1:4, 1:8, etc.) was intraperitoneally administered. The results are summarized in Table 3.

TABLE 3

Effect of BE-12406A on S-180 ascites tumor[1, 2]

| Substance | Dosage, i.p.[3] (mg/kg/injection) | MST[4] (day) | MST[5, 6] (% T/C) |
|---|---|---|---|
| BE-12406A | 40 | >30.0 | >300 |
| | 20 | >30.0 | >300 |
| | 10 | 15.0 | 150 |
| | 5 | 13.0 | 130 |
| | 2.5 | 12.0 | 120 |
| Control Group | 0.25 ml | 10.0 | 100 |

(Footnotes to Table 3)
[1]Inoculum: $10^6$ ascites tumor cells, intraperitoneal
[2]Host: Female ICR mice
[3]Treatment schedule: BE-12406A was administered intraperitoneally on days 1, 4, 7, 9 and 13
[4]MST: Mean survival time (in days)
[5]% T/C: (treated MST/control MST) × 100
[6]Criteria: When % T/C ≧ 125, the test compound was considered to produce a marked antitumor effect at the particular concentration.

With regard to BE-12406A, its acute toxicity in mice (ICR, female) was tested at 100 mg/kg, and no death was found on day 5 after single intraperitoneal dosing.

For the assessment of the inhibitory activity of BE-12406A, B, $X_1$ and $X_2$ against human cancer cells, in vitro tests were carried out. As the test cells, human colon cancer cell lines DLD-1 and LS180 and human lung cancer cell line PC13 were used. The cell culture medium was 10% fetal calf serum-RPMI medium for DLD-1 and LS180, and 10% fetal calf serum-RPMI-1640 medium for PC13. First, each of BE-12406A, B, $X_1$ and $X_2$ was dissolved in dimethyl sulfoxide and the solution was serially diluted with PBS (phosphate-buffered saline) to prepare test solutions. The cancer cell growth inhibition assay was performed as follows. Thus, 100 μl of a cell culture medium containing $3 \times 10^3$ cancer cells was distributed into a 96-well microtiter plate and incubated under 5% $CO_2$ at 37° C. for 24 hours. Then, 11 μl of the above test solutions were added and the incubation was further carried out under 5% $CO_2$ at 37° C. for an additional 72 hours. The cells were then fixed with 50% trichloroacetic acid and stained with 0.4% sulforhodamine B. From the stained cells, the dye was extracted with 10 mM Tris solution and the absorbance at 540 nm was measured and compared with the control. As a result, al of BE-12406A, B, $X_1$ and $X_2$ were found to inhibit the growth of human cancer cells, particularly, BE-12406A and $X_1$ markedly inhibited proliferation of human colon cancer cells LS180 and their 50% inhibitory concentrations ($IC_{50}$) were 12.0 and 36.3 μM, respectively. The above results are summarized in Table 4.

TABLE 4

| Tumor cells | $IC_{50}$ (μM) | | | |
|---|---|---|---|---|
| | BE-12406A | BE-12406B | BE-12406$X_1$ | BE-12406$X_2$ |
| DLD-1 | 18.4 | >220 | 91.9 | >311 |
| LS180 | 12.0 | 88.1 | 36.3 | 311 |
| PC13 | 20.7 | 161 | 115 | >311 |

Thus, the compound (I) of the invention markedly inhibits the growth and multiplication of mouse and human cancer cells. Therefore, the present invention is of value for the treatment of various tumors including leukemia and many tumors such as lung, stomach, colon cancers and others in human and other mammals.

For use as an antitumor drug, the compound of the invention can be supplied in the form of a pharmaceutical composition containing an effective amount of the compound, either alone or in combination with an inert and pharmaceutically acceptable carrier or vehicle.

Such a pharmaceutical composition can be manufactured by using the compound of the invention in combination with an inert and pharmaceutically acceptable carrier and provided in various dosage forms of oral, parenteral or topical administration. Suitable dosage forms include, among others, such solid oral preparations as tablets, capsules, pills, powders, granules, etc. and such liquid preparations for oral, topical or parenteral administration as solutions, suspensions and emulsions. Furthermore, sterile compositions which are extemporaneously reconstituted with sterile water, physiological saline or other sterile solvent for injection can also be provided.

Examples of the pharmaceutically acceptable salt of the compound of the invention are alkali addition salts which can be prepared by adding an equivalent amount of alkali, such as sodium hydroxide, potassium hydroxide or sodium hydrogen carbonate, or an organic amine such as triethylamine, 2-aminoethanol or the like.

The clinically preferred dosage of the compound of the invention depends on the specific compound used, type of formulating agent used, frequency of administration, therapeutic target site, and characteristics of the host and of the tumor. By way of illustration, the daily dosage per adult human is 10 to 500 mg for oral administration and 10 to 100 mg for parenteral, preferably intravenous, administration. The frequency of administration varies with the method of administration and the patient's condition, but generally one to five doses a day are sufficient.

The method for production of BE-12406 is described hereunder.

The microorganisms and mutants thereof, which are used in the production of the antitumor substance BE-12406, are not limited only if they are able to elaborate the antitumor substance BE-12406. By way of example, the strain of microorganism which has the following bacteriological characteristics and was identified as *Streptomyces rutgersensis* subsp. *castelarense* BA-12406 can be employed with advantage.

1. Morphology

The morphological characteristics of this BE-12406-producing strain are as follows.

The well-developed aerial mycelium has not less than 20 terminal spore chains extending spirally or in loops. Neither whirl branching nor fragmentation of hyphae is observed. The spore is sized about 0.2 to 0.5 $\mu m \times 0.3$ to 0.6 $\mu m$ and neither a sporangium nor a sclerotium is formed. The spore surface ornamentation is smooth.

2. Cultural Characteristics on Agar Media (28° C., 14 days)

(1) Sucrose-Nitrate-Agar Medium

The colonies are flat, with the vegetative mycelium being sparse and light yellowish white. No aerial mycelium. No production of soluble pigments.

(2) Glucose-Asparagine-Agar Medium

The colonies are flat, with the vegetative mycelium being good and light yellowish white. No aerial mycelium is formed. No production of soluble pigments.

(3) Glycerin-Asparagine-Agar Medium (ISP-5 Medium)

The colonies are flat, with abundant growth. The vegetative mycelium is tan-brown and the aerial mycelium is abundant, powdery and yellowish brown with a tinge of gray. Some production of a yellowish brown soluble pigment.

(4) Starch-Inorganic Salt-Agar Medium (ISP-4 Medium)

The colonies are flat, with abundant growth. The vegetative mycelium is light tan and the abundant aerial mycelium is powdery and yellowish brown with a tinge of gray. No production of soluble pigments.

(5) Tyrosine-Agar Medium (ISP-7 Medium)

The colonies are slightly wrinkled, with abundant growth. The vegetative mycelium is tan-brown and the abundant aerial mycelium is powdery and yellowish brown with a tinge of gray. Some production of a reddish orange soluble pigment.

(6) Nutrient Agar Medium

The colonies are flat, with abundant light yellowish white vegetative mycelium but no aerial mycelium is formed. No production of soluble pigments.

(7) Yeast-Malt-Agar Medium (ISP-2 Medium)

The colonies are slightly wrinkled, with abundant growth. The vegetative mycelium is blackish brown and the aerial mycelium is abundant, powdery and yellowish brown with a tinge of gray. No production of soluble pigments.

(8) Oatmeal-Agar Medium (ISP-3 Medium)

The colonies are flat, with abundant growth. The vegetative mycelium is gray with a tinge of green and the aerial mycelium is abundant, powdery and yellowish brown with a tinge of gray. No production of soluble pigments.

3. Physiological Characteristics (1) Liquefaction of Gelatin

On glucose-peptone-gelatin medium (incubation temperature, 28° C.), gelatin is liquefied.

(2) Hydrolysis of Starch

On starch-inorganic salt-agar medium (28° C.), starch is hydrolyzed.

(3) Coagulation and Peptonization of Skim Milk

In skim milk medium (28° C.), skim milk is peptonized but not coagulated.

(4) Production of Melanoid Pigments

No production of melanoid pigments on peptone-yeast-iron-agar medium and tyrosine-agar medium or in trypton-yeast liquid medium.

(5) Utilization of Carbohydrates (Pridham-Gottlieb agar, 28° C.)

D-glucose, L-rhamnose, D-fructose and D-galactose are well utilized, D-xylose, L-arabinose, raffinose, D-mannitol an salicin are fairly utilized, and inositol and sucrose are scarcely utilized.

(6) Temperature for Growth

When cultured on modified Bennet's agar medium (1.0% maltose, 0.1% yeast extract, 0.1% beef extract, 0.2% N-Z Amine Type A and 1.6% agar; pH 7.3) at various temperatures of 12° C., 20° C., 28° C., 37° C. and 45° C., the strain grows at all the temperatures below 37° C. The optimal temperature for growth is considered to be about 20° to 28° C.

(7) Tolerance to Sodium Chloride

When incubated on yeast-malt-agar containing sodium chloride at 28° C., the strain grows at NaCl concentrations not exceeding 7%.

4. The Amino Acid Composition of the Cell Wall

LL-Diaminopimelic acid and glycine are detected.

The foregoing bacteriological characteristics suggested that this strain belongs to the genus Streptomyces. Reference to the relevant literature inclusive of Bergey's Manual of Determinative Bacteriology 8th Edition (1974) revealed that this strain is substantially identical with *Streptomyces rutgersensis* subsp. *catelarense*. Accordingly, this strain was designated as *Streptomyces rutgersensis* subsp. *castelarense* BA-12406. This strain has been deposited with the Fermentation Research Institute, Agency of Industrial Science and Technology, Ministry of International Trade and Industry, Japan under the accession number FERM P-10414, after conversion to deposition under the Budapest Treaty, FERM BP-2702.

For the purposes of the present invention, all variants and mutants of BE-12406-producing strains, inclusive of those of the strain described above, may also be employed insofar as they are able to produce antitumor substance BE-12406, and such mutants may be derived from the parent strains by the known techniques such as treatment with X-rays, ultraviolet light or a chemical mutagen, such as nitrogen mustard, azaserine, nitrous acid, 2-aminopurine, N-methyl-N'-nitro-N-nitrosoguanidine (NTG), etc., or the routine transformation techniques such as contacting with phages, transformation, transduction, conjugation and so on.

For the production of BE-12406, the above strain BA-12406, for instance, is cultured in a nutrient medium under aerobic conditions to give a broth containing BE-12406. The nutrients to be included in the medium may be those which are commonly employed in the culture of Streptomyces. Thus, as sources of carbon, there may be employed glucose, glycerol, maltose, starch, sucrose, molasses, dextrin, etc., all of which are readily available from commercial sources. These carbon sources can be used alone or in combination. As sources of nitrogen, there may be mentioned soybean flour, corn steep liquor, meat extract, yeast extract, cottonseed flour, peptone, wheat germ, fishmeal, inorganic ammonium salts, sodium nitrate, etc., all of which are readily available from commercial sources. These nitrogen sources may also be used alone or in combination. As inorganic salts, there may be employed calcium carbonate, sodium chloride, potassium chloride, magnesium sulfate, phosphates, etc., all of which are commercially available. If necessary, trace amounts of heavy metals such as iron., manganese, zinc, molybdenum, capper etc. may also be incorporated in the medium. Moreover, if foaming is copious, an antifoam such as various vegetable oils (e.g. soybean oil, linseed oil, etc.), higher alcohols (e.g. octadecanol etc.) and various silicon compounds may be added to the medium. There can also be employed any other medium components such as 3-(N-morpholino)propanesulfonic acid or sodium borate that will be utilized by the BE-12406-producing strain and contributory to the production of antitumor substance BE-12406.

The cultivation of the BE-12406-producing strain can be carried out by the same procedures as those used generally for the production of microbial metabolites. Thus, whichever of solid culture and liquid culture methods can be employed. For liquid culture, such procedures as stationary culture, stirring culture, shake culture and submerged aerobic culture with agitation can be optionally employed but shake culture and submerged aerobic culture with agitation are particularly preferred. The incubation temperature is 20° C. to 37° C. and preferably 25° C. to 30° C. The preferred medium pH is in the range of 4 to 8 and the incubation period is 24 to 192 hours and preferably 48 to 120 hours.

For harvesting the antitumor substance BE-12406 from the cultured broth, the conventional isolation and purification procedures for microbial metabolites can be selectively employed. Since BE-12406 is produced both intracellularly and extracellularly, it can be recovered from both the cells and the filtrate (supernatant) by the routine procedures such as solvent extraction, ion exchange chromatography, affinity chromatography, partition chromatography, gel filtration, etc., alone or in a suitable combination. High performance liquid chromatography and thin-layer chromatography can also be employed with advantage in the extraction and purification of the product substances.

A preferred method of separation and purification is as follows. The culture broth is first centrifuged to recover the cells, which are then extracted with an organic solvent such as methanol or acetone. This extract is concentrated and subjected to silica gel chromatography using a mixture of chloroform and tetrahydrofuran as the eluent to recover a fraction rich in BE-12406A and a fraction rich in BE-12406A and BE-12406B. Since BE-12406A is crystallized out in the course of concentration of the fraction containing BE-12406A, it can be easily recovered by filtration.

Fractionation of BE-12406A and B can be accomplished by concentrating the fraction containing both BE-12406A and BE-12406B, and subjecting the concentrate to thin-layer chromatography. This thin-layer chromatography can be carried out in the following manner. Thus, a solution of the BE-12406A/B concentrate in a small amount of tetrahydrofuran is applied to a silica gel thin-layer plate and developed with chloroform-methanol. The bands corresponding to BE-12406A and B are respectively scraped off and extracted with methanol. The silica gel is then filtered off and the filtrate is concentrated. The fraction containing BE-12406A and the fraction containing BE-12406B are independently applied to Sephadex LH-20 columns and eluation is carried out with methanol. The eluates are respectively concentrated to give BE-12406A and BE-12406B, both as light yellow crystals.

Another preferred separation and purification procedure is as follows. First, the culture broth is centrifuged to recover the cells and these cells are extracted with an organic solvent such as methanol or acetone. The extract is concentrated and subjected to silica gel chromatography using a mixture of chloroform and methanol as the eluent to recover a fraction containing both BE-12406A and BE-12406X$_1$, a fraction containing both BE-12406X$_1$ and BE-12406X$_2$, and a fraction rich in BE-12406B. Each fraction is concentrated to dryness under reduced pressure and the residue is suspended in methanol. The crystals which separate out are collected by filtration. In this manner, BE-12406A is recovered from the fraction containing both BE-12406A and BE-12406X$_1$, and BE-12406B from the fraction containing BE-12406B. Fractionation of BE-12406X$_1$ and BE-12406X$_2$ can be accomplished by high performance liquid chromatography using Develosil ODS (Yamamura Chemicals Co., Ltd.) or the like as the solid phase. For the purification of BE-12406X$_1$ and BE-12406X$_2$, each fraction is extracted with a solvent or otherwise treated and the solvent is removed. The residue is suspended in methanol and the crystals separating out are recovered by filtration. In this manner, BE-12406X$_1$ can be separated from the BE-12406X$_1$-containing fraction, and BE-12406X$_2$ from the BE-12406X$_2$-containing fraction.

The following examples are merely intended to illustrate the invention in further detail and should by no means be construed to limit its metes and bounds. The present invention should be considered to encompass all modifications of the examples given herein as well as all the known production, concentration, extraction and purification processes which may be applied by those skilled in the art to BE-12406 in view of the properties of BE-12406 disclosed in this specification.

EXAMPLE 1

Four 500 ml conical flasks each containing 100 ml of a culture medium (pH 6.7) composed of 0.1% glucose, 2.0% dextrin, 1.0% corn gluten meal, 0.5% fish meal, 0.1% yeast extract, 0.1% sodium chloride, 0.05% magnesium sulfate, 0.05% calcium chloride, 0.0002% ferrous sulfate, 0.00004% cuprous chloride, 0.00004% manganese chloride, 0.00004% cobalt chloride, 0.00008% zinc sulfate, 0.00008% sodium borate, 0.00024% ammonium molybdate, and 0.5% 3-(N-morpholino)propanesulfonic acid were inoculated with BA-12406 grown on an agar slant and each flask was incubated on a rotary shaker (180 r.p.m.) at 28° C. for 72 hours. One-milliliter aliquots of the culture were inoculated into 150 conical flasks of 500 ml capacity each containing 100 ml of the same medium as above and incubated on a rotary shaker (180 r.p.m.) at 28° C. for 120 hours. The resulting broth (15 was filtered and the cells were washed with 500 ml of deionized water, followed by addition of 4.5 of methanol. The mixture was stirred at room temperature for 1 hour and filtered to give a methanol extract. The methanol extraction was repeated and about 9 of the methanol extracts combined was concentrated to about 800 ml. The residue was extracted with 5 l of ethyl acetate and the extract was concentrated. The residue was extracted with about 250 ml of tetrahydrofuran and the insolubles were filtered off. The filtrate was concentrated to give 8.2 g of a crude substance containing both BE-12406A and B. This crude product was dissolved in 500 ml of chloroform-tetrahydrofuran (3:2 v/v) and the solution was passed through a silica gel chromatographic column (6.5×37 cm) using chloroform-tetrahydrofuran (1:1 v/v) as the eluent. In this chromatography, BE-12406A emerged faster from the silica gel column than BE-12406B and this BE-12406A fraction was concentrated to isolate 671 mg of BE-12406A as pale yellow crystals.

The subsequent elution with the same eluent gave a fraction containing both BE-12406B and BE-12406A. This fraction was concentrated to give 280 mg of a BE-12406A/B complex.

Using 14.4 mg of the BE-12406 complex thus obtained, thin-layer chromatography was carried out using a silica gel plate (20×20 cm, Merck, U.S.) and, as the developer, a 5:1 v/v mixture of chloroform and methanol. The silica gel in the area corresponding to BE-12406B was scraped off and extracted with methanol. The extract was concentrated and subjected to column chromatography on Sephadex LH-20 (1.5×120 cm, Pharmacia) using methanol as the eluent. The BE-12406B fraction was concentrated to give 5.1 mg of BE-12406B as light yellow crystals.

EXAMPLE 2

A 500 ml conical flask containing 100 ml of a medium (pH 6.7) composed of 0.1% glucose, 2.0% dextrin, 1.0% corn gluten meal, 0.5% fish meal, 0.1% yeast extract, 0.1% sodium chloride, 0.05% magnesium sulfate, 0.05% calcium chloride, 0.0002% ferrous sulfate, 0.00004% cupric chloride, 0.00004% manganese chloride, 0.00004% cobalt chloride, 0.00008% zinc sulfate, 0.00008% sodium borate, 0.00024% ammonium molybdate and 0.5% 3-(N-morpholino)propanesulfonic acid was inoculated with BA-12406 grown on an agar slant and the flask was incubated on a rotary shaker (200 r.p.m.) at 28° C. for 24 hours. A 100 ml portion of this seed culture was inoculated into a 30 l jar fermenter containing 20 l of the same medium as above and incubated under submerged aerobic conditions of 20 l/min aeration, 300 r.p.m. and 28° C. for 80 hours.

The pH of the resulting culture broth (18 l) was adjusted to 3.0 with 3N hydrochloric acid and the broth was filtered to recover the cells. The cells were extracted with 18 of methanol and the extract was concentrated under reduced pressure to about 2 l. This concentration residue was diluted with 2.5 of deionized water and 10 l of ethyl acetate and the pH of the aqueous layer was adjusted to 8.5 with 3N sodium hydroxide solution. The ethyl acetate layer (9.5 l) was concentrated under reduced pressure and the residue was extracted with 300 ml of n-hexane to give 4.82 g of precipitate. This precipitate was dissolved in 250 ml of methanol-tetrahydrofuran (1:1 v/v) and then added in silica gel (Wakogel C-300, Wako Pure Chemical Industries Co., Ltd.). The mixture was dried under reduced pressure. The product-silica gel mixture was applied to a silica gel chromatographic column (4×35 cm, Wakogel C-300), and elution was carried out with chloroform and chloroform-methanol. This elution was first carried out using 2 l of chloroform and, then, gradient elution was carried out using 2 l of chloroform-methanol (30:1 v/v) and 2 l of chloroform-methanol (10:1 v/v). Then, elution was further carried out with 1 l of chloroform-methanol (10:1 v/v) and finally 1 l of chloroform-methanol (4:1). The first eluate (1.5 l) containing both BE-12406A and X$_1$ was concentrated to dryness under reduced pressure and the residue was suspended in about 75 ml of methanol. The resulting precipitate was collected by filtration to give 665 mg of BE-12406A. As the next eluate from the silica gel chromatographic column, 1 l of a fraction containing both BE-12406X$_1$ and X$_2$ was obtained. This fraction was concentrated to dryness under reduced pressure and suspended in methanol, and the resulting precipitate was collected by filtration to give 94 mg of a crude powder containing both BE-12406X$_1$ and X$_2$. The mother liquor obtained in the above procedure was chromatographed on Toyopearl HW-40F (3 cm×50 cm, Toso Co., Ltd.) and elution was carried out with methanol to give 125 ml of a fraction containing BE-12406X$_1$. This fraction was concentrated to dryness under reduced pressure and the residue was suspended in about 50 ml of methanol. The resulting precipitate was recovered to give 13 mg of BE-12406X$_1$. As the last eluate from the silica gel chromatographic column, 1.5 l of a fraction containing BE-12406B was obtained. This fraction was concentrated to dryness under reduced pressure and the solid residue was suspended in about 50 ml of methanol. The resulting precipitate was recovered to give 116 mg of BE-12406B. Then, 94 mg of the above-mentioned crude substance containing both BE-12406X$_1$ and X$_2$ was subjected to high performance liquid chromatography on Develosil ODS (5×50 cm, Yamamura Chemical Co., Ltd.) and eluation was carried out with acetonitrile-0.01M monopotassium phosphate (60:40 v/v; pH 4.5) at a flow rate of 100 ml/min. During the retention time from 70 to 80 minutes, a fraction containing BE-12406X$_2$ was obtained. This fraction was concentrated to 1.0 under reduced pressure and the residue was adjusted to pH 3.0 with 3N-hydrochloric acid and extracted with 3 l of ethyl acetate. The ethyl acetate layer was concentrated to dryness under reduced pressure and suspended in about 60 ml of methanol and the resulting precipitate was collected by filtration to give 49 mg of BE-12406X$_2$.

As described hereinbefore, the antitumor substance BE-12406 according to the present invention inhibits not only sensitive tumor cells but also those tumor cells resistant to the existing anticancer drugs in equal degrees and is, therefore, useful as a therapeutic agent for cancer in the field of medicine. Furthermore, BE-12406 is useful as a starting material for other anticancer agents as well.

While the invention has been described in detail and with reference to specific embodiments thereof, it will be apparent to one skilled in the art that various changes and modifications can be made therein without departing from the spirit and scope thereof.

What is claimed is:

1. An antitumor substance or a pharmaceutically acceptable salt thereof, which is represented by the general formula

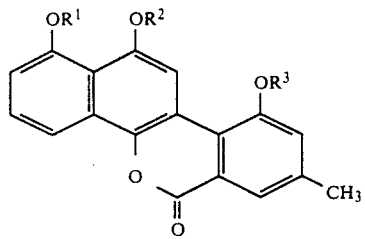

(I)

wherein R$^1$ and R$^2$, which may be the same or different, each represents a hydrogen atom or a group of the formula

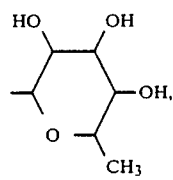

and R$^3$ represents a hydrogen atom or a methyl group.

2. An antitumor substance or a pharmaceutically acceptable salt thereof as claimed in claim 1, wherein R$^1$ is a hydrogen atom, R$^2$ is a group of the formula

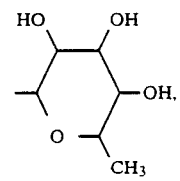

and R$^3$ is a methyl group.

3. An antitumor substance or a pharmaceutically acceptable salt thereof as claimed in claim 1, wherein R$^1$ is a hydrogen atom, R$^2$ is a group of the formula

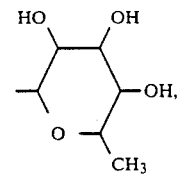

and R$^3$ is a hydrogen atom.

4. An antitumor substance or a pharmaceutically acceptable salt thereof as claimed in claim 1, wherein R$^1$ is a group of the formula

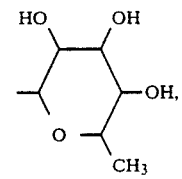

R$^2$ is a hydrogen atom, and R$^3$ is a methyl group.

5. An antitumor substance or a pharmaceutically acceptable salt thereof as claimed in claim 1, wherein R$^1$ is a hydrogen atom, R$^2$ is a hydrogen atom, and R$^3$ is a methyl group.

6. An antitumor agent which comprises effective amount of an antitumor substance or a pharmaceutically acceptable salt thereof, which is represented by the general formula

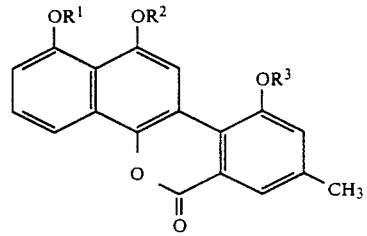

(I)

wherein R$^1$ and R$^2$, which may be the same or different, each represents a hydrogen atom or a group of the formula

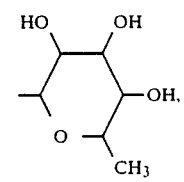

and R$^3$ represents a hydrogen atom or a methyl group; and a pharmaceutically acceptable carrier.

* * * * *